US008828938B2

(12) United States Patent
Zhang et al.

(10) Patent No.: US 8,828,938 B2
(45) Date of Patent: Sep. 9, 2014

(54) METHOD FOR THE MANUFACTURE OF DEGARELIX

(75) Inventors: Haixiang Zhang, Strasbourg (FR); Jens Fomsgaard, Farum (DK); Gunnar Staerkaer, Fredriksberg C (DK)

(73) Assignee: Polypeptide Laboratories A/S, Hillerod (DK)

( * ) Notice: Subject to any disclaimer, the term of this patent is extended or adjusted under 35 U.S.C. 154(b) by 193 days.

(21) Appl. No.: 13/265,402

(22) PCT Filed: Apr. 26, 2010

(86) PCT No.: PCT/EP2010/002550
§ 371 (c)(1),
(2), (4) Date: Oct. 20, 2011

(87) PCT Pub. No.: WO2010/121835
PCT Pub. Date: Oct. 28, 2010

(65) Prior Publication Data
US 2012/0041172 A1 Feb. 16, 2012

(30) Foreign Application Priority Data
Apr. 24, 2009 (SE) ...................... 0900558

(51) Int. Cl.
C07K 7/23 (2006.01)
(52) U.S. Cl.
CPC ...................... C07K 7/23 (2013.01)
USPC ...................... 514/10.3
(58) Field of Classification Search
CPC ...................... C07K 7/23
See application file for complete search history.

(56) References Cited

U.S. PATENT DOCUMENTS

| 5,925,730 | A | 7/1999 | Semple et al. | |
|---|---|---|---|---|
| 2006/0247177 | A1* | 11/2006 | Millar | 514/15 |
| 2007/0041902 | A1* | 2/2007 | Goodman et al. | 424/1.69 |

FOREIGN PATENT DOCUMENTS

WO    WO-98/46634    10/1998

OTHER PUBLICATIONS

Hachmann et al. "Alternative to Piperidine in Fmoc Solid-Phase Synthesis," J. Comb. Chem. 2006, 8, 149.*
International Search Report, mailed Sep. 22, 2010.
Kaneti, J., et al.; "Thorpe-Ingold effects in cyclizations to five-membered and six-membered rings containing planar segments. The rearrangement of N(1)-alkyl-substituted dihydroorotic acids to hydantoinacetic acids in base"; Organic and Biomolecular Chemistry; Royal Society of Chemistry GB; vol. 2, No. 7; Apr. 7, 2004; pp. 1098-1103.
Cescato Renzo, et al.; "Design and in vitro characterization of highly sst2-selective somatostatin antagonists suitable for radiotargeting"; Journal of Medicinal Chemistry; Jul. 10, 2008; vol. 51, No. 13; pp. 4030-4037.
Thomas E. Creighton, "Proteins Structures and Molecular Properties" Second Edition, European Molecular Biology Laboratory, Heidelberg, Germany, (1993), p. 45, col. 1, line 20—p. 47, col. 1, line 21.
Theodora W. Greene et al.; "Protective Groups in Organic Synthesis", Second Edition, John Wiley & Sons, Inc., (1991), p. 318.
Botond Penke, et al.; "Solid-Phase Synthesis of Peptide Amides on a Polystyrene Support Using Fluorenylmethoxycarbonyl Protecting Groups"; J. Org. Chem., 1987, vol. 53, pp. 1197-1200.
L.A. Sorbera, et al.; "Degarelix Acetate GnRH Antagonist Prostate Cancer Therapy"; Drugs of the Future 2006, 31(9), pp. 755-766.
Jose Kaneti, et al.; "Thorpe-Ingold effects in cyclizations to five-membered and six-membered rings containing planar segments. The rearrangement of N(1)-alkyl-substituted dihydroorotic acids to hydantoinacetic acids in base"; Org. Biomol. Chem., 2004, 2, pp. 1098-1103.
Manoj P. Samant et al.; "Iterative Approach to the Discovery of Novel Degarelix Analogues: Substitutions at Positions 3, 7, and 8. Part II"; J. Med. Chem., 2005, vol. 48, pp. 4851-4860.
Guangcheng Jiang et al.; "GnRH Antagonists: A new Generation of Long Acting Analogues Incorporating p-Ureido-phenylalanines at Positions 5 and 6"; J. Med. Chem., 2001, vol. 44, pp. 453-467.
Manoj P. Samant et al.; "Novel Analogues of Degarelix Incorporating Hydroxy-, Methoxy-, and Pegylated-Urea Moieties at Positions 3, 5, 6 and the N-Terminus. Part III[1], 2"; J. Med. Chem. 2006, vol. 49, pp. 3536-3543.
Asen H. Koedjikov, et al.; "β-Ureido Acids and Dihydrouracils. Part 15.[1] Effect of Allylic Strain on Ring Opening of 1,6-Disubstituted Dihydrouracils"; J. Chem. Coc. Perkin Trans. II, 1984, pp. 1077-1081.
CN 101284863 A, Jier Biochemistry Shanghai Co Ltd, Oct. 15, 20085, (abstract) Retrieved from: WPI database, Week 200911, AN 2009-839047.
International-Type Search Report from Swedish Patent Office for ITS/SE09/00124, date of mailing Oct. 21, 2009.

* cited by examiner

*Primary Examiner* — Christina Bradley
(74) *Attorney, Agent, or Firm* — Dickstein Shapiro LLP

(57) ABSTRACT

In a step-wise synthesis of degarelix comprising 0.3% by weight or less of 4-([2-(5-hydantoyl)]acetylamino)-phenylalanine analog on (solid support)-$NH_2$ a step comprises providing a solution of an amino acid or peptide of which the α-amino group is protected by Fmoc; contacting the support with the solution in the presence of reagent for forming a peptide bond between a carboxyl group of the amino acid or peptide and (solid support)-$NH_2$; removing Fmoc by contacting the support with an organic base, in particular piperidine, in an organic solvent. Also disclosed is degarelix of high purity prepared by the method of the invention and the use of Fmoc in the synthesis of degarelix.

15 Claims, No Drawings

METHOD FOR THE MANUFACTURE OF DEGARELIX

FIELD OF THE INVENTION

The present invention relates to a method for the manufacture of synthetic peptides, in particular to the manufacture of the decapeptide degarelix.

BACKGROUND OF THE INVENTION

There are a number of known methods available for peptide synthesis. A classical approach is liquid-phase peptide synthesis (LPPS), which has been a preferred method for producing large quantities of peptides. Another current and commonly used approach for peptide synthesis is solid-phase peptide synthesis (SPPS), wherein the growing peptide chain is covalently attached to a resin on a solid support, until cleaved from it once the desired length and sequence is achieved. In these methods reactive side chains of the incorporated amino acids need to be protected in order to avoid other reactions apart from the desired formation of new peptide bonds in the growing peptide. In addition, to avoid side reactions between the added amino acids, as well as incorporation of multiple amino acids in each step, the added amino acids are normally α-amino protected. The synthesis thus becomes one of repeated cycles of deprotection of the α-amine of a solid-phase attached peptide, followed by coupling to a single, α-amino protected amino acid unit.

Degarelix is a GnRH antagonist for use in the treatment of prostate cancer. Degarelix has an immediate onset of action and suppresses gonadotropins, testosterone, and prostate-specific antigen (PSA). Degarelix is a synthetic decapeptide of the formula Ac-D-2Nal-D-Phe(4Cl)-D-3 Pal-Ser-4Aph(Hor)-D-4Aph(Cbm)-Leu-ILys-Pro-D-Ala-NH$_2$.

The fifth amino acid moiety from the amino terminal of degarelix corresponds to the non-natural amino acid Aph(L-Hor). Aph(L-Hor) stands for (L-hydroorotyl)-4-amino-phenylalanine. It is known in the art (Koedjikov, A. H. et. al., J. Chem. Soc. Perkin, Trans. 2, 1984, pages 1077-1081; Kaneti, J. et. al., Org. Biomol. Chem., 2004, pages 1098-1103) that, under basic conditions, compounds comprising a dihydrouracil moiety undergo rearrangement to compounds comprising a hydantoin moiety. The corresponding rearrangement of Aph/L-Hor) is illustrated below (upper left: dihydrouracil moiety N-4-(L-hydroorotylamino)-phenylalanine I, R=—CH$_2$CHNH$_2$COOH; lower right: hydantoin moiety II, N-4-[2-(5-hydantoyl)-acetyl)-phenylalanine).

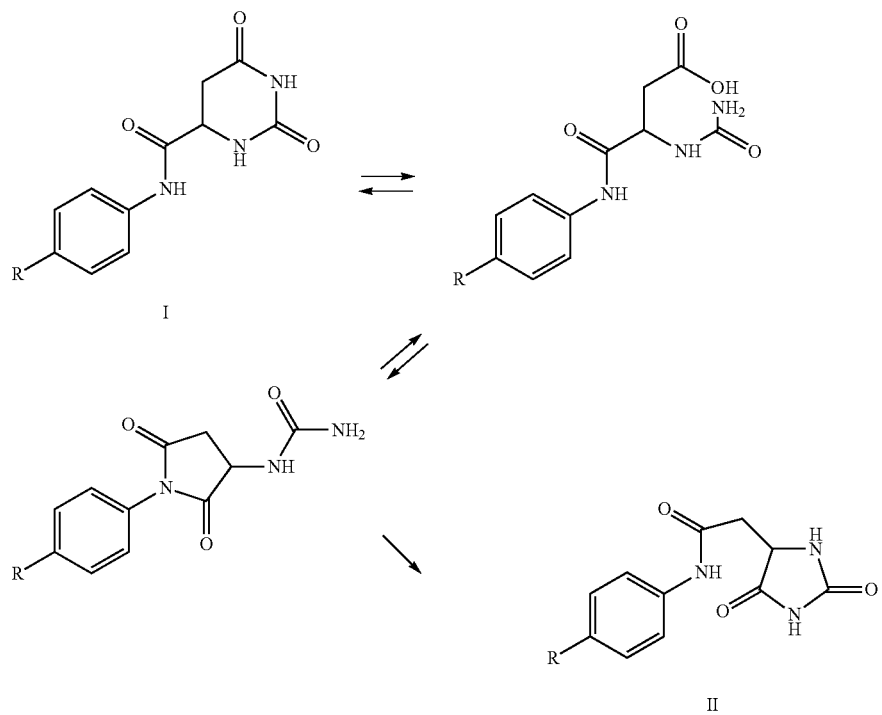

In the rearrangement, the dihydrouracil moiety I is converted to a hydantoin moiety II. The L-Hor moiety of 4Aph(L-Hor) being of the dihydrouracil kind such rearrangement is expected to occur during a process of manufacture of degarelix in which basic conditions are employed. This was confirmed by the applicant by contacting peptide synthesis intermediates comprising α-amino group Fmoc-protected terminal 4Aph(Hor) with either NaOH or the organic base dicyclohexyl amine (DCHA). The deprotection product obtained was found to be contaminated by up to several % by weight of the corresponding hydantoin rearrangement product. In the synthesis of degarelix the intermediate Fmoc-4Aph(Hor)-4Aph(Cbm)-Leu-ILys-Pro-D-Ala-NH-Resin thus can be expected to be partially rearranged to Fmoc-X-4Aph(Cbm)-Leu-ILys-Pro-D-Ala-NH-Resin, X being 4-([2-(5-hydantoyl)]acetylamino)-phenylalanine when deprotected under basic conditions. Consequently, a degarelix product obtained via Fmoc-4Aph(Hor)-4Aph(Cbm)-Leu-ILys-Pro-D-Ala-NH-Resin thus can be expected to be contaminated by a corresponding amount of Ac-D-2Nal-D-Phe(4Cl)-D-3 Pal-Ser-X-D-4Aph(Cbm)-Leu-ILys-Pro-D-Ala-NH$_2$. Degarelix is the active ingredient of a drug for administration to humans. Therefore it must not be contaminated by any impurity exceeding 0.3% by weight of the product. Thus, in degarelix suited for human consumption the hydantoin by-product cannot be tolerated in an amount of more than 0.3 by weight. Since the hydantoin-moiety containing by-product is structurally very similar to degarelix, their separation is difficult. If attempted, separation is expected to result in substantial loss of product. Hence, in a process of manufacture of pharmaceutical-grade degarelix employing the protecting group Fmoc, basic conditions should be avoided.

The synthesis of degarelix is disclosed in U.S. Pat. No. 5,925,730A. The preferred α-amino protecting group in this synthesis and which has been used in all Examples is the tert-butyloxy-carbonyl group (Boc). In addition a wide range of other well-known protecting groups, such as the fluorenylmethyloxycarbonyl group (Fmoc) are disclosed for this purpose. An advantage with the Boc group is that α-amino groups protected by it can be deblocked under acidic conditions by standard treatment with trifluoroacetic acid (TFA). A disadvantage with TFA is its high human toxicity, which puts manufacturing personnel at risk. Another disadvantage with TFA is its environmental toxicity, which either makes it disposure costly or, if disposed improperly, contaminates the environment.

OBJECTS OF THE INVENTION

It is an object of the invention to provide a method for the manufacture of degarelix, which does not put human health at risk, in particular which is less hazardous to human health than the method disclosed in U.S. Pat. No. 5,925,730A.

It is another object of the invention to provide a method for the manufacture of degarelix, which does not put the environment at risk, in particular which is less hazardous to the environment than the method disclosed in U.S. Pat. No. 5,925,730A.

It is an additional object of the invention to provide a method for the manufacture of degarelix, which is less costly than methods known in the art.

Further objects of the invention will become apparent from the following summary of the invention, a number of preferred embodiments disclosed in form of examples, and the appended claims.

SUMMARY OF THE INVENTION

The inventors have surprisingly found that pharmaceutically pure degarelix can be manufactured by solid phase synthesis using Fmoc as α-amino protecting group. "Pharmaceutically pure" indicates the product does not contain more than 0.3% by weight of any single impurity. Unexpectedly the Aph(L-Hor) moiety does not undergo rearrangement during solid-phase synthesis in spite of being subjected to several cycles of Fmoc protection and deprotection under basic conditions.

Fmoc α-amino-protected amino acids are coupled to the resin and then to one another in a step-wise, cyclic and sequence-dependent manner. Each step of coupling of an amino acid is followed by a step of deprotection to remove the Fmoc protection group and allow for the next amino acid to be coupled. Deprotection is achieved by base. Preferably the base piperidine or alkyl-substituted piperidine in an organic media is used for deprotection.

Side-chain protection is preferably included to protect side chains of amino acids which are particularly reactive or labile, to avoid side reactions and/or branching of the growing molecule. The side chain protection groups are removed once the full length of the growing peptide has been achieved.

Thus, according to the present invention is disclosed a method of manufacture of degarelix, Ac-D-2Nal-D-Phe(4Cl)-D-3 Pal-Ser-4Aph(Hor)-D-4Aph(Cbm)-Leu-ILys-Pro-D-Ala-NH$_2$, wherein degarelix comprises 0.3% by weight or less, in particular 0.1% by weight or less, most particularly 0.01% by weight or less, of Ac-D-2Nal-D-Phe(4Cl)-D-3 Pal-Ser-X-D-4Aph(Cbm)-Leu-ILys-Pro-D-Ala-NH$_2$, wherein X is 4-([2-(5-hydantoyl)]-acetylamino)-phenylalanine, the method comprising step-wise synthesis on a solid support comprising an amino group linked to the support, wherein a step comprises providing a solution of an amino acid or peptide of which an α-amino group is protected by Fmoc; contacting the support with the solution in the presence of reagent for forming a peptide bond between a carboxyl group of the dissolved amino acid or peptide and the amino group linked to the support for a time sufficient to form said peptide bond; removing Fmoc by contacting the support with an organic base in an organic solvent. A preferred organic base is piperidine. Other preferred organic bases are C-alkyl substituted piperidines, in particular 2-alkylpiperidine, 3-alkylpiperidine, 2,4-dialkylpiperidine, 2,5-dialkyl-piperidine, 2,6-dialkylpiperidine, wherein alkyl is branched or straight chain from 1 to 6 carbon, in particular methyl or ethyl, most particularly methyl. A preferred solvent is dimethyl formamide. Another preferred solvent is diethyl formamide. Other preferred solvents are NMP or DMA. A preferred reagent for forming a peptide bond comprises N,N'-diisopropylcarbodiimide. It is preferred for the amino group linked to the support to be an α-amino group of a fragment of degarelix linked to the support. It is also preferred for the peptide protected by Fmoc to be a fragment of degarelix. A preferred support is one selected from Rink amide AM resin and Rink amide MBHA resin. A preferred method for releasing degarelix from the support is by acid treatment.

According to a preferred aspect of the invention is disclosed degarelix prepared by the method of the invention comprising 0.3% by weight or less of Ac-D-2Nal-D-Phe(4Cl)-D-3 Pal-Ser-X-D-4Aph(Cbm)-Leu-ILys-Pro-D-Ala-NH$_2$, wherein X is 4-([2-(5-hydantoyl)]-acetylamino)-phenylalanine, in particular 0.1% by weight or less, most particularly 0.01% by weight or less.

According to another preferred aspect of the invention is disclosed the use of Fmoc in solid phase synthesis for preparing degarelix containing 0.3% by weight or less, more preferred 0.1% by weight or less, most preferred 0.01% by weight or less, of Ac-D-2Nal-D-Phe(4Cl)-D-3 Pal-Ser-X-D-4Aph(Cbm)-Leu-ILys-Pro-D-Ala-NH$_2$, wherein X is (4-[2-(5-hydantoyl)]acetylamino)-phenylalanine.

The invention will now be described in greater detail by reference to a drawing and a number of preferred embodiments described in examples.

DESCRIPTION OF PREFERRED EMBODIMENTS

Abbreviations 4-(2',4'-Dimethoxyphenyl-Fmoc-aminomethyl)-phenoxyacetamidomethyl polystyrene resin [Fmoc-Rink amide AM-resin]

4-(2',4'-Dimethoxyphenyl-Fmoc-aminomethyl)-phenoxyacetamido-4-methylbenzhydrylamine polystyrene resin [Fmoc-Rink amide-MBHA resin]

9-Fluorenylmethyloxycarbonyl-D-4-chlorophenylalanine [Fmoc-D-Phe-(4Cl)—OH]

9-Fluorenylmethyloxycarbonyl-D-2-naphtylalanine [Fmoc-D-2Nal-OH]

9-Fluorenylmethyloxycarbonyl-D-3-pyridylalanine [Fmoc-D-3 Pal-OH]
9-Fluorenylmethyloxycarbonyl-N(4)-(t-butylcarbamoyl)-D-4-aminophenylalanine [Fmoc-D-4Aph(tBuCbm)-OH]
9-Fluorenylmethyloxycarbonyl-N(4)-(L-hydroorotyl)-4-aminophenylalanine [Fmoc-Aph(L-Hor)-OH]
9-Fluorenylmethyloxycarbonyl-leucine-OH [Fmoc-L-Leu-OH]
9-Fluorenylmethyloxycarbonyl-O-t-butyl-serine [Fmoc-Ser(tBu)—OH]
9-Fluorenylmethyloxycarbonyl-L-proline [Fmoc-Pro-OH]
9-Fluorenylmethyloxycarbonyl-D-alanine [Fmoc-D-Ala-OH]
9-Fluorenylmethyloxycarbonyl-N(s)-isopropyl-[Fmoc-L-ILys(Boc)-OH]
N($\epsilon$)-Boc-lysine
Acetonitrile
2-Propanol (isopropanol) (IPA)
Ethanol, 99.9% (EtOH)
Methanol (MeOH)
Purified water (water)
Ethyl acetate (AcOEt)
Acetic acid (AcOH)
Aqueous ammonium hydroxide (Aq. $NH_3$)
Ammonium acetate ($AcONH_4$)
Acetyl imidazole
N-methylmorpholine (NMM)
N-methylpyrrolidone (NMP)
N,N'-diisopropylcarbodiimide (DIC)
N,N-dimethylformamide (DMF)
N,N-dimethylacetamide (DMA)
Dimethyl sulphoxide (DMSO)
Dicyclohexyl amine (DCHA)
1-Hydroxybenzotriazole (HOBt)
Sodium hydroxide solution, aqueous (Aq. NaOH)
Hydrochloric acid, aqueous (Aq. HCl)
Phosphoric acid ($H_3PO_4$)
Trifluoroacetic acid (TFA)
Diisopropyethylamine (DIEA)
Ethanedithiol (EDT)
Isopropylethylether (IPE)
In-Process-Control (IPC)
Benzyl-oxycarbonyl (Z)
1,8-Diazabicyclo[5.4.0]-undec-7-ene (DBU)

Example 1

Hydantoin Formation in the Synthesis of Degarelix

The rearrangement of the hydroorotic group to a hydantoinacetyl group in the production of degarelix has been seen at two stages and two sets of basic conditions.

The first rearrangement appeared during basic extractions of the segment Z-Ser(tBu)-4Aph(Hor)-D-4Aph(tBu-Cbm)-Leu-ILys(Boc)-Pro-D-Ala-$NH_2$. The pH was adjusted to 9.1 in the organic/aqueous two-phase system using conc. NaOH solution, resulting in the formation of 4.5% by weight of the hydantoin analogue. The mechanism appeared to comprise two steps: (a) hydrolysis of the 6-membered hydroorotic moiety under basic conditions followed by ring closure to the 5-membered hydantoin analogue under acidic conditions.

The second rearrangement was observed during evaporation of the segment Z-Ser(tBu)-4Aph(Hor)-D-4Aph(tBu-Cbm)-Leu-OH.DCHA. After the preceding extractions, Z-Ser(tBu)-4Aph(Hor)-D-4Aph(tBu-Cbm)-Leu-OH was dissolved in a mixture of ethyl acetate and 2-butanol. DCHA (2.5 eq.) was added because the segment is isolated as the DCHA salt after evaporation of the solvent followed by a precipitation step. In the particular batch both the hydantoin analogue and the hydrolysed form (mentioned above) were identified. Quantification of the hydantoin was not possible because poor separation by HPLC from other products; the hydrolyzed form was formed in an amount of 1.34% by weight of the combined products. Experimental evidence showed that the amount of rearrangement/hydrolysis was related to the amount of DCHA used in the method.

The following experiment provided further proof of the instability of the hydrooroic moiety under basic conditions. Z-Ser(tBu)-4Aph(Hor)-D-4Aph(tBu-Cbm)-Leu-OH.DCHA (67 mM) was dissolved in wet 2-BuOH with 167 mM (2.5 eq) DCHA at 31° C. After 25 h, 1.3% of the hydantoin analogue and 0.3% of the hydrolysed intermediate had been formed.

Example 2

Stability of Degarelix in DBU/DMF and Piperidine/DMF

The stability of degarelix was tested under conditions corresponding to those used for removal of the Fmoc-group during SPPS. The hydroorotic group in the side chain of 4Aph(Hor), amino acid residue no. 5 in the sequence of degarelix, is known to be sensitive to base and rearrange to a hydantoinacetyl group. All SPPS procedures known to the inventors had been based on Boc-chemistry.

Samples of degarelix were dissolved in 20% piperidine/DMF; 2% DBU in DMF, and 2% DBU+5% water in DMF; respectively. The samples were analysed by HPLC after 20 h and the amount of the hydantoin analogue determined.

2% DBU/DMF resulted in the formation of 1.8% hydantoin. If 5% water was present, too (simulating wet DMF), the amount was increased to 7%. Surprisingly, the use of 20% piperidine in DMF did not result in any formation of the hydantoin analogue, indicating that this mixture might be useful for Fmoc-based SPPS of Degarelix.

Example 3

Synthesis and Purification of Degarelix Using Fmo-/Rink Amide AM Resin

Step 1. Fmoc-Rink amide AM resin (64 g; substitution 0.67 mmol/g) was placed in a reactor and washed with 1.9 L DMF. To the swollen resin 250 ml of 20% piperidine in DMF is added and stirred for 20 min. The reactor is emptied through the filter in the bottom by applying vacuum to the reactor and a second treatment with 250 ml 20% piperidine in DMF is performed for 20 min. The reactor is once again emptied by applying vacuum to it followed by a wash of the peptide resin using 2 L of DMF. The reactor is then emptied by applying vacuum. The peptide resin is now ready for step 2.

Step 2. A solution of 27.0 g Fmoc-D-Ala-OH (2 eq.), 14.3 g HOBt and 13.2 ml DIC is dissolved in 250 ml of DMF and allowed to activate for 15 min, after which it is poured into the reactor containing the peptide resin. After 1 h of reaction time, 2.2 ml of NMM is added to the solution and the reaction is allowed to proceed for another hour. Then 30 ml acetic acid anhydride and 2 ml NMM is added to the mixture, which is allowed to stand under stirring for 15 min. Then the reactor is emptied by using vacuum. The peptide resin is washed with 2 L DMF. After applying vacuum to the reactor, removing the DMF, the peptide resin is treated with 250 ml of 20% piperidine in DMF for 20 min. The reactor is emptied by applying vacuum and a second treatment of 250 ml 20% piperidine in DMF for 20 min is performed. The reactor is once again emptied by applying vacuum and the peptide resin is washed with 2 L of DMF. It is now ready for step 3.

Step 3. A solution of 29 g Fmoc-L-Pro-OH (2 eq), 14.3 g HOBt and 13.2 ml DIC is dissolved in 250 ml DMF and allowed to activate for 25 min, after which it is poured into the reactor containing the peptide resin. After 75 min of reaction, 2.2 ml NMM is added to the solution, and the reaction is allowed to proceed for another hour. Then 30 ml acetic acid anhydride and 2 ml NMM is added to the mixture, which is allowed to stand under stirring for 15 min, The reactor is then emptied by using vacuum. DMF (2.6 L) is used for washing the peptide resin. After applying vacuum to the reactor, removing the DMF, the peptide resin is treated with 250 ml of 20% piperidine in DMF for 20 min. The reactor is emptied by applying vacuum, and a second treatment with 250 ml 20% piperidine in DMF for 20 min is performed. The reactor is once again emptied by applying vacuum and the peptide resin is washed with 2 L of DMF. It is now ready for step 4.

Step 4. A solution of 33 g Fmoc-L-ILys(Boc)-OH (1.5 eq), 10.7 g HOBt and 10.1 ml DIC is dissolved in 250 ml of DMF and allowed to activate for 0.5 h, after which it is poured into the reactor containing the peptide resin. After 2 h of reaction, 2.2 ml NMM is added to the solution and the reaction is allowed to proceed for another hour. Then 30 ml acetic acid anhydride and 2.2 ml NMM is added to the mixture, which is allowed to stand under stirring for 15 min, whereupon the reactor is emptied by using vacuum. The peptide resin is washed with DMF (3 L). After applying vacuum to the reactor, removing the DMF, the peptide resin is treated with 250 ml of 20% piperidine in DMF for 20 min. The reactor is emptied by applying vacuum and a second treatment of 250 ml 20% piperidine in DMF for 20 min is performed. The reactor is once again emptied by applying vacuum and the peptide resin is washed with 3.5 L DMF. It is now ready for step 5.

Step 5. A solution of 38 g Fmoc-L-Leu-OH (2.5 eq), 18 g of HOBt and 16.8 ml of DIC is dissolved in 250 ml of DMF and allowed to activate for 0.5 h, after which it is poured into the reactor containing the peptide resin. After 2 h of reaction, 2.2 ml NMM is added to the solution, and the reaction is allowed to proceed for another 50 min. Then 30 ml acetic acid anhydride and 2 ml NMM is added to the mixture, which is allowed to stand under stirring for 15 min. Then the reactor is emptied by using vacuum. DMF (2.6 L) is used for washing the peptide resin. After applying vacuum to the reactor, removing the DMF, the peptide resin is treated with 250 ml of 20% piperidine in DMF for 20 min. The reactor is emptied by applying vacuum and a second treatment with 250 ml 20% piperidine in DMF for 20 min is performed. The reactor is once again emptied by applying vacuum and the peptide resin is washed with 2.5 L of DMF. It is now ready for step 6.

Step 6. A solution of 32 g of Fmoc-D-4Aph(tBu-Cbm)-OH (1.5 eq), 10.7 g HOBt and 10.1 ml DIC is dissolved in 250 ml of DMF and allowed to activate for 1 hour, after which it is poured into the reactor containing the peptide resin. After 20 min of reaction, 22 ml NMM is added to the solution and the reaction is allowed to proceed for another 20 h. Then 30 ml acetic acid anhydride and 2 ml NMM is added to the mixture, which is allowed to stand under stirring for 15 min. Then the reactor is emptied by using vacuum. The peptide resin is washed with 4 L DMF. After applying vacuum to the reactor, removing the DMF, the peptide resin is treated with 250 ml of 20% piperidine in DMF for 20 min. The reactor is emptied by applying vacuum and a second 20 min treatment with 250 ml 20% piperidine in DMF is performed. The reactor is once again emptied by applying vacuum and the peptide resin is washed with 3.4 L DMF. It is now ready for step 7.

Step 7. A solution of 35 g Fmoc-L-4Aph(L-Hor)-OH (1.5 eq), 11 g HOBt and 10.1 ml DIC is dissolved in 350 ml DMF and allowed to activate for 1 h, after which it is poured into the reactor containing the peptide resin. After 50 min of reaction, 2.2 ml NMM is added to the solution and the reaction is allowed to proceed for another 21.5 h. The reactor is emptied by using vacuum. The peptide resin is washed with 4.4 L DMF. After applying vacuum to the reactor, removing the DMF, the peptide resin is treated with 350 ml of 20% piperidine in DMF for 20 min. The reactor is emptied by applying vacuum and a second 20 min treatment with 350 ml 20% piperidine in DMF is performed. The reactor is once again emptied by applying vacuum and the peptide resin is washed with 4.4 L DMF. It is now ready for step 8.

Step 8. Fmoc-L-Ser(tBu)—OH (2.5 eq) (41 g), 17.9 g HOBt, 16.8 ml DIC and 4.9 ml of NMM is dissolved in 500 ml of DMF and poured into the reactor containing the peptide resin. The reaction is allowed to proceed for 3.5 h. The reactor is then emptied by using vacuum. The peptide resin is washed with 4.2 L DMF. After applying vacuum to the reactor, removing the DMF, the peptide resin is treated with 375 ml of 20% piperidine in DMF for 20 min. The reactor is emptied by applying vacuum and a second 20 min treatment of 375 ml 20% piperidine in DMF is performed. The reactor is once again emptied by applying vacuum and the peptide resin washed with 4.2 L of DMF. It is now ready for step 9.

Step 9. A solution of 25 g Fmoc-D-3 Pal-OH (1.5 eq), 10.7 g HOBt, 10.1 ml DIC and 4.9 ml NMM is dissolved in 400 ml of DMF and poured into the reactor containing the peptide resin. The reaction is allowed to proceed for 4.5 h. Then the reactor is emptied by using vacuum. The peptide resin is washed with 4.2 L DMF. After applying vacuum to the reactor, removing the DMF, the peptide resin is treated with 375 ml of 20% piperidine in DMF for 20 min. The reactor is emptied by applying vacuum and a second 20 min treatment with 375 ml 20% piperidine in DMF is performed. The reactor is once again emptied by applying vacuum and the peptide resin washed with 4.2 L of DMF. It is now ready for step 10.

Step 10. A solution of 27 g Fmoc-D-Phe(4Cl)—OH (1.5 eq), 10.7 g HOBt, 10.1 ml DIC and 4.9 ml NMM is dissolved in 400 ml of DMF and is poured into the reactor containing the peptide resin. The reaction is allowed to proceed for 10 h. The reactor is emptied by using vacuum. The resin is washed with 5.5 L DMF. After applying vacuum to the reactor and removing the DMF, the peptide resin is treated with 375 ml of 20% piperidine in DMF for 20 min. The reactor is emptied by applying vacuum and a second 20 min treatment with 375 ml 20% piperidine in DMF is performed. The reactor is once again emptied by applying vacuum and the peptide resin washed with 5 L DMF. It is now ready for step 11.

Step 11. A solution of 28 g Fmoc-D-2Nal-OH (1.5 eq), 10.7 g HOBt, 10.1 ml DIC and 4.9 ml NMM is dissolved in 400 ml DMF and poured into the reactor containing the peptide resin. The reaction is allowed to proceed for 2.5 h. The reactor is emptied by using vacuum. The peptide resin is washed with 5.2 L DMF. After applying vacuum to the reactor and removing the DMF, the peptide resin is treated with 375 ml of 20% piperidine in DMF for 20 min. The reactor is emptied by applying vacuum and a second 20 min treatment of 375 ml 20% piperidine in DMF is performed. The reactor is once again emptied by applying vacuum and the peptide resin washed with 5 L DMF. It is now ready for and is ready for step 12.

Step 12. Acetylimidazole (3 eq) (14.5 g) and 4.9 ml NMM is dissolved in 400 ml DMF and poured into the reactor. After 1.5 h, the reactor is emptied by applying vacuum to the reactor. The peptide resin is washed with 5 L DMF and the reactor emptied using vacuum.

Step 13. The peptide resin is washed with WA and dried under vacuum. Peptide resin (129.8 g; yield 96%) was isolated.

Step 14. Dry peptide resin (60 g) is suspended in 600 ml TFA for 25 h at room temperature. It was then poured into a mixture of 2.4 L water, 620 g ammonium acetate, 600 ml ethanol and 600 ml acetic acid. The mixture is adjusted to a pH between 3 and 4 using TFA and filtered.

Step 15. The product is purified using a two step purification protocol. In the first step a column (2.5 cm×34 cm) packed with reversed phase C-18 material is used with a buffer system consisting of buffer A (0.12% aqueous TFA) and buffer B (99.9% ethanol) A volume from the filtered solution from step 14 corresponding to 1.6 g of the product is applied to the column. Purification is executed using a step gradient starting with 10% B for 2-3 column volumes, 29% B for 5-7 column volumes and a gradient from 29% B to 50% B over 3 column volumes at a flow rate of 70 ml/min. This procedure is followed until all the filtered solution from step 14 has been processed. All fractions collected are analyzed by analytical HPLC. Fractions containing product with a purity higher than 94% are pooled. The second purification step is performed using a column (2.5 cm×34 cm) packed with reverse phase C-18 material and a buffer system consisting of a buffer A (1% aqueous acetic acid), buffer B (99.9% ethanol), and buffer C (0.5 M aqueous ammonium acetate). From the pooled fractions containing the product an amount equivalent to 1.3 g of the product is applied to the column and purification performed by applying a step gradient starting with 10% B+90% C for 2-3 column volumes followed by 90% A+10% B for 2-3 column volumes. The product is eluted by 24% B+76% A. The fractions containing product with the acceptable purity are pooled and desalted using the same column. Desalting is performed using buffer A (1% aqueous acetic acid) and buffer B (99.9% ethanol). A volume from the pooled purified fraction corresponding to 1.6 g of product is applied to the column, 2-3 column volumes buffer A being used to wash out any ammonium acetate in the product. Then the product is eluted using 50% buffer A+50% buffer B. The solution of the purified product containing 50% ethanol is concentrated on a rotary evaporator. When all the ethanol has been removed the remaining solution containing the product is lyophilized. A total of 11.8 g (overall yield 37%) of degarelix is obtained as a fluffy solid. 4-([2-(5-Hydantoyl)]acetylamino)-phenylalanine could not be detected in the product (HPLC).

Example 4

Synthesis and Purification of Degarelix Using Fmoc-Rink Amide MBHA

Performed substantially as the synthesis and purification of Example 1. Deviations from the method of Example 1:
a) Fmoc-D-Aph(Cbm)-OH was used instead of Fmoc-D-Aph(tBu-Cbm)-OH;
b) Acetylation of the N-terminal of H-D-2-Nal-peptide-resin was performed using acetic acid anhydride instead of acetylimidazole;
c) Acetonitrile was used in purification instead of ethanol.

4-([2-(5-Hydantoyl)]acetylamino)-phenylalanine could not be detected in the product by HPLC.

The invention claimed is:

1. A method of manufacture of degarelix, Ac-D-2Nal-D-Phe(4Cl)-D-3Pal-Ser-4Aph(Hor)-D-4Aph(Cbm)-Leu-ILys-Pro-D-Ala-NH2, wherein Aph is 4-amino-phenylaniline, (Hor) is (L-hydroorotyl), and (Cbm) is (carbamoyl), containing 0.3% by weight or less of Ac-D-2Nal-D-Phe(4Cl)-D-3Pal-Ser-X-D-4Aph(Cbm)-Leu-ILys-Pro-D-Ala-NH2, wherein X is 4-([2-(5-hydantoyl)]acetylamino)-phenylalanine, comprising step-wise providing a solution of an amino acid or peptide in which an α-amino group is protected by Fmoc; contacting a solid support having an amino group linked thereto with the solution in the presence of reagent which forms a peptide bond between a carboxyl group of the dissolved amino acid or peptide and the amino group linked to the support for a time sufficient to form said peptide bond; removing Fmoc by contacting the support with an organic base selected from the group consisting of piperidine and C-alkyl substituted piperidine, wherein the alkyl is branched or straight chained and has from 1 to 6 atoms, in an organic solvent.

2. The method of claim 1, wherein the organic base is piperidine.

3. The method of claim 1, wherein the organic solvent is dimethyl formamide.

4. The method of claim 1, wherein the reagent for forming a peptide bond comprises N,N'-diisopropylcarbodiimide.

5. The method of claim 1, wherein the amino group linked to the support is an α-amino group of a fragment of degarelix.

6. The method of claim 1, wherein the solution contains a fragment of degarelix protected by Fmoc.

7. The method of claim 1, wherein the support is selected from the group consisting of 4-(2',4'-dimethoxyphenyl-Fmoc-aminomethyl)-phenoxyacetamido-norleucylaminomethyl resin and 4-(2',4'-dimethoxyphenyl-Fmoc-aminomethyl)phenoxyacetamido-methylbenzhydryl amide resin.

8. The method of claim 1 further comprising releasing degarelix from the support by acid treatment.

9. The method of claim 1, wherein the C-alkyl substituted piperidine is selected from the group consisting of 2-alkyl-piperidine, 3-alkylpiperidine, 2,4-dialkylpiperidine, 2,5-dialkyl-piperidine, and 2,6-dialkylpiperidine.

10. The method of claim 2, wherein the organic solvent is dimethyl formamide.

11. The method of claim 10, wherein the reagent for forming a peptide bond comprises N,N'-diisopropylcarbodiimide.

12. The method of claim 11, wherein the amino group linked to the support is an α-amino group of a fragment of degarelix.

13. The method of claim 12, wherein the solution contains a fragment of degarelix protected by Fmoc.

14. The method of claim 13, wherein the support is selected from the group consisting of 4-(2',4'-dimethoxyphenyl-Fmoc-aminomethyl)-phenoxyacetamido-norleucylaminomethyl resin and 4-(2',4'-dimethoxyphenyl-Fmoc-aminomethyl)phenoxyacetamido-methylbenzhydryl amide resin.

15. The method of claim 14 comprising releasing degarelix from the support by acid treatment.

* * * * *